(12) United States Patent  
Kang et al.

(10) Patent No.: US 10,130,460 B2  
(45) Date of Patent: Nov. 20, 2018

(54) STENT HAVING EXTERIOR PATH

(71) Applicant: S&G BIOTECH, INC., Seongnam-si, Gyeonggi-do (KR)

(72) Inventors: Sung Kwon Kang, Yongin-si (KR); So Hee Jung, Seoul (KR); Young Jae Lee, Gwangju (KR); Jong Kyun Lee, Seoul (KR)

(73) Assignee: S&G BIOTECH, INC., Seongnam-si, Gyeonggi-do (KR)

( * ) Notice: Subject to any disclaimer, the term of this patent is extended or adjusted under 35 U.S.C. 154(b) by 0 days.

(21) Appl. No.: 15/321,081

(22) PCT Filed: Oct. 20, 2014

(86) PCT No.: PCT/KR2014/009837  
§ 371 (c)(1),  
(2) Date: Dec. 21, 2016

(87) PCT Pub. No.: WO2015/199289  
PCT Pub. Date: Dec. 30, 2015

(65) Prior Publication Data  
US 2017/0151051 A1     Jun. 1, 2017

(30) Foreign Application Priority Data  
Jun. 26, 2014   (KR) .................. 10-2014-0078707

(51) Int. Cl.  
*A61F 2/04* (2013.01)  
*A61F 2/07* (2013.01)  
(Continued)

(52) U.S. Cl.  
CPC ............... *A61F 2/04* (2013.01); *A61F 2/07* (2013.01); *A61F 2/90* (2013.01);  
(Continued)

(58) Field of Classification Search  
CPC .... A61F 2/0013; A61F 2/0027; A61F 2/0036; A61F 2/06; A61F 2002/068;  
(Continued)

(56) References Cited

U.S. PATENT DOCUMENTS 5,129,910 A * 7/1992 Phan ................ A61B 17/22031  
604/264  
5,282,847 A * 2/1994 Trescony ................. A61F 2/06  
623/1.29  
(Continued)

FOREIGN PATENT DOCUMENTS

CN       201108514 Y      9/2008  
CN       102387761 A      3/2012  
(Continued)

OTHER PUBLICATIONS

In'l Search Report dated Feb. 13, 2015 in Int'l Application No. PCT/KR2014/009837.  
(Continued)

*Primary Examiner* — Alvin Stewart  
(74) *Attorney, Agent, or Firm* — Panitch Schwarze Balisario & Nadel LLP

(57) ABSTRACT

A stent according to the present invention includes: a stent main body that has a plurality of holes formed in the surface thereof and a circumferential part of which the inside is hollow; and a cover that covers one side of the outer circumferential surface of the stent main body, in which the stent main body has an exterior path that provides a channel through which the body fluid secreted from a diverging duct can flow along the longitudinal direction of the stent main body to the outside of the cover.

7 Claims, 12 Drawing Sheets

(51) Int. Cl.
*A61F 2/90* (2013.01)
*A61F 2/06* (2013.01)

(52) U.S. Cl.
CPC ... *A61F 2002/041* (2013.01); *A61F 2002/068* (2013.01); *A61F 2002/072* (2013.01); *A61F 2220/005* (2013.01); *A61F 2230/0004* (2013.01)

(58) Field of Classification Search
CPC ...... A61F 2002/821; A61F 2/844; A61F 2/82; A61F 2/945; A61F 2/94; A61F 2/90; A61F 2/02; A61F 2/04; A61F 2002/047; A61F 2002/048
USPC ............... 623/1.25, 1.27, 1.29, 23.66, 23.65
See application file for complete search history.

(56) References Cited

U.S. PATENT DOCUMENTS

| | | | | |
|---|---|---|---|---|
| 5,607,468 | A * | 3/1997 | Rogers | A61F 2/07 128/898 |
| 5,653,745 | A * | 8/1997 | Trescony | A61F 2/06 623/1.29 |
| 5,989,207 | A * | 11/1999 | Hughes | A61M 27/008 604/8 |
| 6,053,943 | A * | 4/2000 | Edwin | A61F 2/07 600/36 |
| 6,214,037 | B1 * | 4/2001 | Mitchell | A61F 2/07 623/1.11 |
| 6,626,938 | B1 * | 9/2003 | Butaric | A61F 2/064 623/1.13 |
| 6,776,194 | B2 * | 8/2004 | Houston | A61F 2/06 138/108 |
| 7,150,758 | B2 * | 12/2006 | Kari | A61F 2/06 623/1.25 |
| 7,220,237 | B2 * | 5/2007 | Gannoe | A61B 17/072 128/898 |
| 7,238,199 | B2 * | 7/2007 | Feldman | A61F 2/82 623/1.15 |
| 7,314,483 | B2 * | 1/2008 | Landau | A61F 2/064 623/1.16 |
| 7,338,530 | B2 * | 3/2008 | Carter | A61F 2/07 623/23.66 |
| 7,815,591 | B2 * | 10/2010 | Levine | A61F 2/04 604/8 |
| 8,167,927 | B2 * | 5/2012 | Chobotov | A61F 2/07 623/1.13 |
| 8,252,064 | B2 * | 8/2012 | Shalaby | A61F 2/90 604/8 |
| 8,696,738 | B2 * | 4/2014 | Noesner | A61F 2/07 623/1.32 |
| 9,867,727 | B2 * | 1/2018 | Chobotov | A61F 2/958 |
| 2002/0058986 | A1 | 5/2002 | Landau et al. | |
| 2002/0179166 | A1 * | 12/2002 | Houston | A61F 2/06 138/39 |
| 2004/0122507 | A1 * | 6/2004 | Henderson | A61F 2/06 623/1.27 |
| 2005/0080478 | A1 * | 4/2005 | Barongan | A61B 17/32072 623/1.14 |
| 2006/0259113 | A1 * | 11/2006 | Nissl | A61F 2/04 623/1.3 |
| 2007/0270939 | A1 * | 11/2007 | Hood | A61F 2/82 623/1.22 |
| 2010/0030321 | A1 * | 2/2010 | Mach | A61F 2/07 623/1.18 |
| 2010/0100170 | A1 * | 4/2010 | Tan | A61F 2/94 623/1.18 |
| 2010/0256731 | A1 * | 10/2010 | Mangiardi | A61B 17/7233 623/1.15 |
| 2011/0288628 | A1 * | 11/2011 | Noesner | A61F 2/07 623/1.15 |
| 2012/0029625 | A1 | 2/2012 | Chobotov et al. | |
| 2013/0018448 | A1 * | 1/2013 | Folan | A61F 2/958 623/1.11 |
| 2013/0218259 | A1 | 8/2013 | Quinn | |
| 2014/0243992 | A1 * | 8/2014 | Walsh | A61F 2/04 623/23.7 |

FOREIGN PATENT DOCUMENTS

| | | |
|---|---|---|
| JP | 2001327609 A | 11/2001 |
| JP | 2005211293 A | 8/2005 |
| JP | 5328046 B2 | 10/2013 |
| WO | 2011059222 A2 | 5/2011 |

OTHER PUBLICATIONS

Extended Search Report dated Feb. 5, 2018 EP Application No. 14895684.0.

* cited by examiner

STENT HAVING EXTERIOR PATH

CROSS-REFERENCE TO RELATED APPLICATION

This application is a Section 371 of International Application No. PCT/KR2014/009837, filed Oct. 20, 2014, which was published in the Korean language on Dec. 30, 2015, under International Publication No. WO 2015/199289 A1, and the disclosure of which is incorporated herein by reference.

TECHNICAL FIELD

The present invention relates to a stent and, more particularly, to a stent that allows for easy flow of body fluid, such as blood and pancreatin, by expanding ducts such as a bile duct, a blood vessel, or a pancreatic duet, that allows body fluid to flow inside and outside the stent by having an external path allowing body fluid, which comes from divergent ducts such as divergent blood vessels, intrahepatic bile ducts, or pancreatic duets from cystic ducts, to flow through, ducts, and that can reduce friction on a diseased part by flexibly bending to fit to the shapes of ducts.

BACKGROUND ART

In general, when duets that require a predetermined inner diameter, such as blood vessels, the esophagus, the pancreatic duct, or the bile duct, are constricted due to various reasons such as deposits or when there is a need for an operation, a stent that can artificially expand the constricted portion is inserted.

The circumferential parts of a stent need to be smoothly constricted and expanded in order to be easily inserted into a duct. To this end, stents are made of twisting a plurality of wires or a plurality of holes are formed through stents by a laser pattern. Accordingly, when a stent is inserted into a constricted portion, the tissues of the constricted portion protrude into the stent through the holes by pressure due to expansion of the stent. In particular, when a stent is installed in a duct for a long period of time or when the pressure due to expansion of a stent increased over a predetermined level, side effects such as injury or necrosis of the tissues of the narrowed portion may be generated.

Accordingly, various methods for solving these problems have been proposed. A method of forming a membrane to close the holes of a stent is representative of the methods.

A plurality of wires is twisted to form a stent, so a plurality of rectangular holes is formed through the surface. Further, the entire stent is coated with silicon etc. to close the holes in order to prevent the tissues of the installation portion from protruding into the stent. Accordingly, the stent can be stably fixed at the port ion and it is possible to prevent the tissues from protruding into the stent.

As described above, in order to close the holes of a stent, generally, there is a method of dipping a stent in liquid-state silicon or a method of manufacturing a film of silicon or polyurethane, covering a stent with the film, and then fixing both ends of the film to the stent using a suture.

However, according to the method of using dipping, a stent is entirely covered with silicon, so when the stent is inserted into a curved portion such as a digestive system, a strong restoring force for returning to the initial state acts. That is, the stent is not sufficiently flexible, so it may cause inflammation by generating friction on the diseased part.

According to the method of using a film, it is required to go through an additional biological test to obtain medical sanction on sutures, in addition to the stent, and there is a need for the additional process of fixing a film to the stent using a suture, it takes more costs and time to manufacture the stent.

Further, when a stent is entirely covered by the method of using dipping or a film, body fluid such as blood or pancreatin can smoothly flow inside the stent, but the body fluid flowing into a duct through a divergent duct such as intrahepatic bile ducts or pancreatic ducts cannot smoothly flow.

In order to solve these problems, a method of partially close the holes of a stent has been proposed, but the problem that tissues protrude into the stent through the holes still remains.

DISCLOSURE

Technical Problem

In order to solve the problems, an object of the present invention is to provide a stent that allows for easy flow of body fluid, such as blood and pancreatin, by expanding ducts such as a bile duct, a blood vessel, or a pancreatic duct, that allows body fluid to flow inside and outside the stent by having an external path allowing body fluid, which comes from divergent ducts such as divergent blood vessels, intrahepatic bile ducts, or pancreatic ducts from cystic ducts, to flow through ducts, and that can reduce friction on a diseased part by flexibly bending to fit to the shapes of ducts.

However, the objects of the present invention are not limited to those stated above and other objects not stated above may be clear to those skilled in the art from the following description.

Technical Solution

In order to achieve the objects of the present invention, a stent includes: a stent main body that has a plurality of holes formed in the surface thereof and an outer circumferential part of which the inside is hollow; and a cover that covers one side of the outer circumferential surface of the stent main body, in which the stent main body has an exterior path that provides a channel through which the body fluid secreted from a diverging duct can flow along the longitudinal direction of the stent main body to the outside of the cover.

The external path may be formed by a recession on a side of the circumferential part of the stent main body and the recession is formed along the longitudinal direction of the stent main body, so that the body fluid secreted from the diverging duct may flow through the recession.

The external path may be formed by a projection on a side of the circumferential part of the stent main body and the projection may be formed along the longitudinal direction of the stent main body, so that the body fluid secreted from the diverging duet may flow through a spaced space formed between the duct and the stent main body by the projection.

A plurality of external paths may be provided.

The external path may be formed by recessions and projections repeatedly formed along the circumferential part of the stent main body and the recessions and the projections may be formed along the longitudinal direction of the stent main body, so that the body fluid secreted from the diverging duct may flow through spaced spaces formed between the duct and the stent main body by the difference in diameter of the recessions and the projections.

At least any one end of both ends of the stent main body may expand further than the center portion to prevent separation.

The cover may include: a film for covering a side of the outer peripheral surface of the stent main body; and a coating layer formed to coat both ends of the stent and fix the film to the stent main body.

The coating layer may fee formed at both ends of the stent main body to a depth where an end of the film is overlapped at a predetermined portion and is hardened to fix both ends of the film to the stent main body.

Advantageous Effects

The stent of the present invention has the following effects.

First, it is possible to allow body fluid coming out of a diverging duct to flow on the outer side of the stent into a duct, using the external path having various cross-sections.

Second, it is possible to prevent the tissues of a constricted portion from protruding into the stent through the holes formed through the stent when the holes are closed by a film and a coating layer.

Third, since a film is disposed at the center portion of the stent main body, the stent can easily bend in accordance with movement of an operator of curved portion of a duct.

Fourth, it is possible to remarkably reduce discomfort that the patient feels due to the stent.

Fifth, since the film and the coating may be made of various materials, it is possible to easily maintaining the bending state by adjusting friction.

Sixth, since the film is fixed by the coating layer that functions as an adhesive, it is possible to fix the film even without using a suture.

The effects of the present invention are not limited to those described above and other effects not stated herein may be made apparent to those skilled in the art from claims.

DESCRIPTION OF DRAWINGS

The accompanying drawings show exemplary embodiments of the present invention and are provided to help understanding the spirit of the present invention together with the detailed description of the present invention, so the present invention should not be construed as being limited to those shown in the drawings.

MODE FOR INVENTION

Hereinafter, exemplary embodiments of the present invention will, be described in detail with reference to the accompanying drawings.

Figure 1:
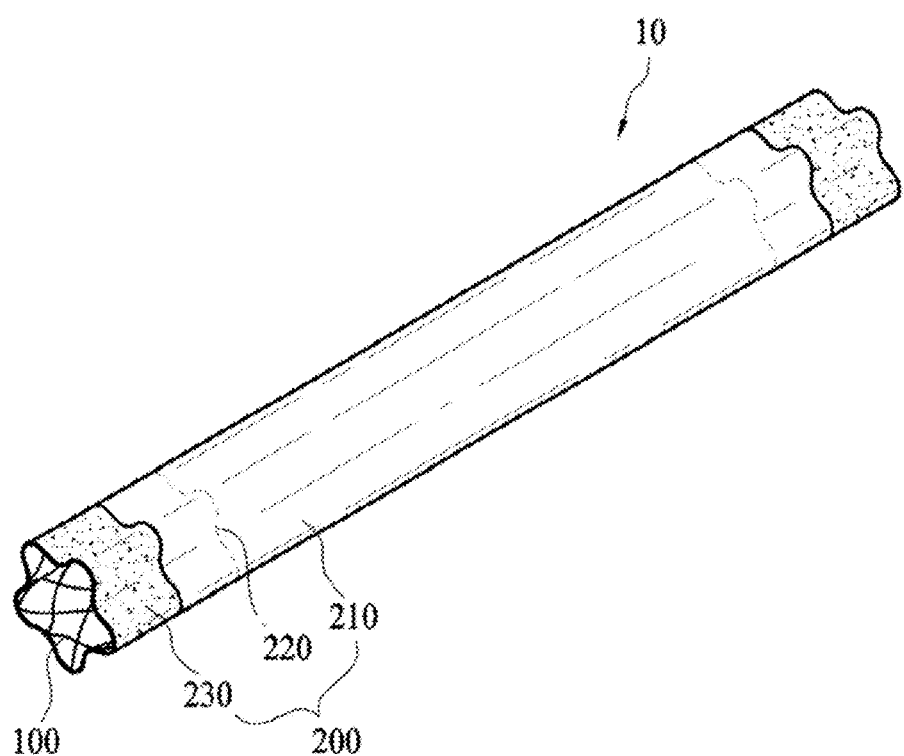
FIG. 1 is a perspective view showing a stent according to the present invention.

FIG. 1 is a perspective view showing a stent according to an embodiment of the present invention. A stent 10 according to the present invention, as shown in FIG. 1, largely includes a stent main body 100 and a cover 200 that, closes holes formed through the stent main body 100 by covering a side of the outer peripheral surface of the stent main body 100.

The stent main body 100 has a circumferential part of which the inside is hollow and the circumferential part is formed by twisting a plurality of wires or by a laser pattern. By twisting a plurality wires or by a laser pattern, a plurality of holes is formed in the surface of the stent main body 100.

That is, since the circumferential part of the stent main body 100 is configured by twisting a plurality of wires or by a laser pattern such that a plurality of holes is formed, it can easily contract or expand. Further, it can stably expand the inner wall and form a space through which, body fluid such as blood or pancreatin can smoothly flow when installed at a constricted portion.

In detail, the stent main body 100 of the present invention is formed by twisting wires and the circumferential part has generally a circular cross-section. This is not for forming corners to prevent the stent 10 from stimulating the tissues of an installation portion.

Further, the circular cross-section of the stent main body 100 of the present invention is formed in a circular shape, in which a projection or a recession is formed on a side and, the projection or the recession extends along the longitudinal direction of the entire stent main body 100 to be able to provide a space through which body fluid spouting from a diverging duct 510 can flow.

Further, a lasso (not shown) is disposed at any one end of both ends of the stent main body 100 to easily remove the stent 10 later. The lasso is generally used in this art, so the detailed description, is not provided.

An external path 300 may be formed along the longitudinal direction of the stent main body 100 in various cross-sectional shapes and the configuration such as the shape of the external path 300 is described in detail in each of the following embodiments.

An expanding portion (not shown) having a larger area than the center may be formed at any one end of both ends of the stent main body 100. That is, as the expanding portion is formed, the stent 10 can be stably fixed at an installation portion in a duct 500.

The expanding portion may be formed to fee stepped from the center or may be inclined as it goes to the outside by a slope. If the expanding portion is formed to be stepped, a plurality of steps may be formed such that the area gradually increases as it goes to the outside, and in this case, it is possible to reduce foreign substance feeling that the patient feels due to the stent 10.

The cover 200 covers a side of the outer peripheral surface of the stent main body 100 to prevent the tissues at a constricted portion from protruding into the stent 10 through the holes of the surface of the stent 10 by closing the holes formed in the surface of the stent main body 100. The cover 200 may be any types of covers that are used in the related art as long as they can achieve the purpose described above.

However, it is preferable to use a film 210 and a primary coating layer 220 together in order to flexibly bend in accordance with the shape of the duct 500.

The film 210 covers a side of the outer peripheral surface of the stent main body 100, preferably, the entire of the stent main body 100 to close the holes of the stent main body 100. Any film may be used for the film 210 as long as it can achieve the purpose described above. However, it is preferable to manufacture a pipe-shaped film 210 having an inner diameter corresponding to the outer diameter of the stent main body 100 by covering cloth, synthetic resin, rubber, silicon, or polyurethane of the outer peripheral surface of a rod made of PTFE (Polytetrafluoroethylene/ Teflon).

The method of manufacturing the film 210 is just an embodiment and not limited and any film that is generally used in the related art can be used for the film 210.

Further, the length of the film 210 may be shorter than or the same as the length of the stent main body 100.

The primary coating layer 220 is formed at one side of the stent main body 100, preferably, to overlap a predetermined length of both, ends of the film 210 at both ends of the stent main body 100, thereby coupling and fixing the film 210 to the stent main body 100 and forming a layer on a side of the stent main body 100 where the film 210 is not disposed. The layer is made of a hermetic material such as silicon, and the primary coating layer 220 is formed by a dipping process that exposes and dips the stent main body 100 in liquid-state silicon or a method of spraying silicon with a spray.

A secondary coating layer 230 may be additionally formed on the outer peripheral surfaces of both ends of the film 210 by a spray or a brush or may be formed by dipping, similar to the primary coating layer 220, in order to more stably bond the film 210 bonded by the primary coating layer 220 to the stent main body 100. The secondary coating portion 231 may be smaller than or the same in length as the primary coating portion 221.

A process of fixing and coupling the film 210 to the stent main, body 100 through the primary coating layer 220 and the secondary coating layer 230 is briefly described hereafter.

Figure 2:
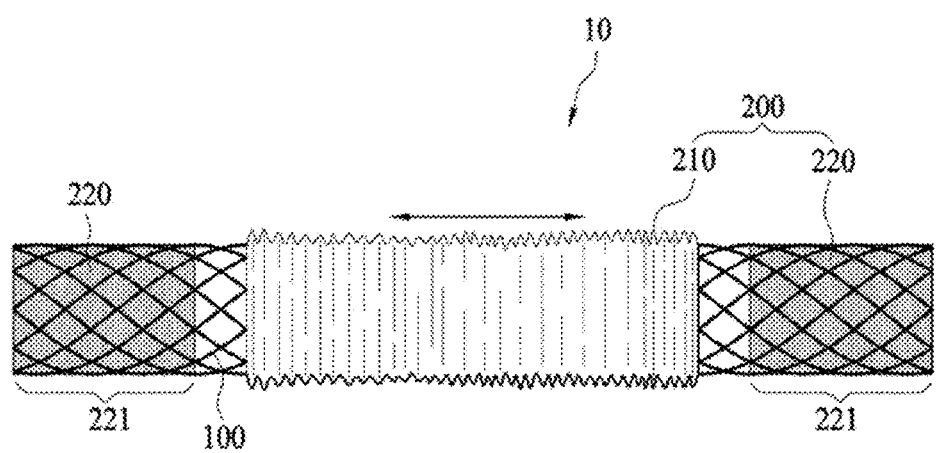
FIGS. 2 to 4 are side views showing a process of coupling a film to a stent main body according to the present invention.
Figure 3:
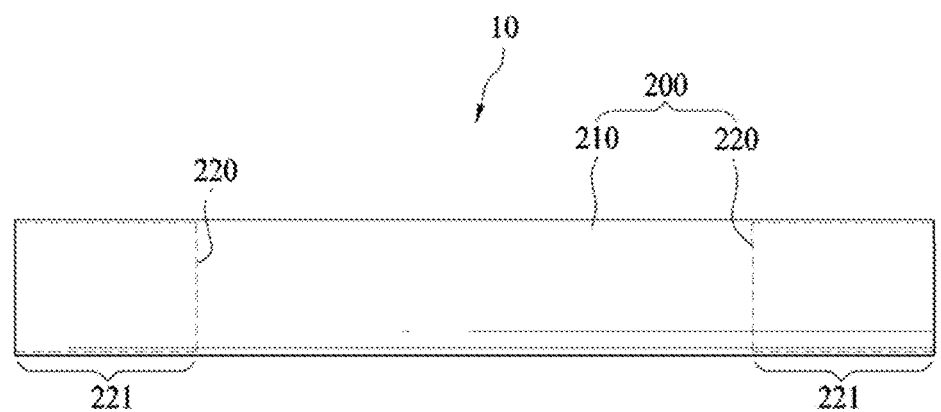
Figure 4:
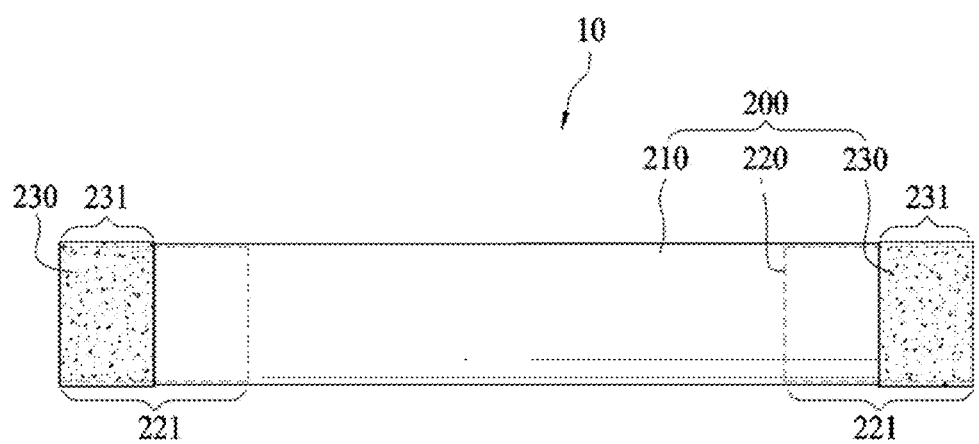

FIGS. 2 to 4 are side views showing a process of coupling a film to a stent main body according to the present invention. First, as shown in FIG. 2, the stent main body 100 is inserted into the film 210 such that the stent main body 100 passes through the film 210. Thereafter, the film 210 is folded to the center portion of the stent main body 100. Depending on the use, the film 210 may not be folded to the center portion of the stent main body 100, but may be pushed to an end of the stent main body 100.

Thereafter, both ends of the stent main body 100 are coated by dipping them into liquid-state silicon or polyurethane. The primary coating portions 221 formed at both ends of the stent main body 100 is formed such that a portion of both ends of the film 210 can overlap. That is, the non-coated portion of the stent main body 100 should be shorter than the film 210.

Next, as shown in FIG. 3, both ends of the film 210 pushed to the center or an end of the stent main body 100 are spread to overlap the primary coating portions 221 formed at both ends of the stent main body 100. This process should be performed before the primary coating portions 221 are all hardened.

The film 210 is arranged such that both ends of the film 210 overlap the primary coating portions 221 formed at both ends of the stent main body 100, and then, the first coating portions 221 are hardened so that the primary coating layer 220 is formed. As described above, in the process of hardening the primary coating portions 221 to form the primary coating layer 220, the film 210 is fixed to a side of the stent main body 100 by the primary coating layer 220 that is an adhesive.

Finally, as shown in FIG. 4, the secondary coating layers 230 are formed on the outer peripheral surfaces of both ends of the film 210 bonded to the stent main body 100 through the primary coating layer 220, thereby more firmly coupling the film 210 to the stent main body 100. Coating liquid the same as or different from the primary coating layer 220 may be used for the secondary coating layer 230, depending on the use.

Figure 5:
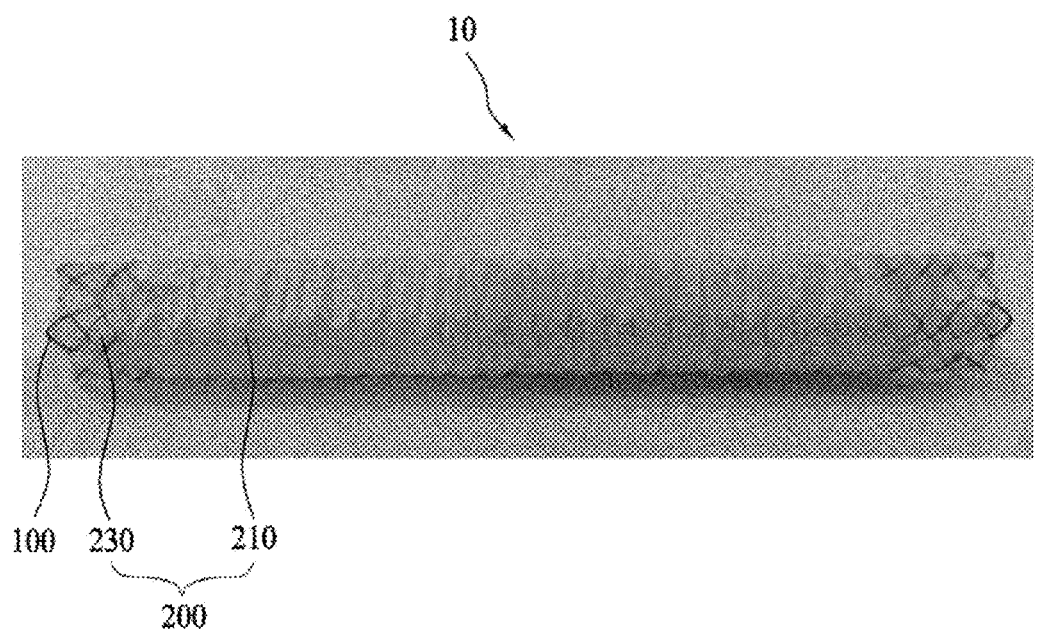
FIGS. 5 and 6 are pictures showing/perspective views of a stent according to the present invention.
Figure 6:
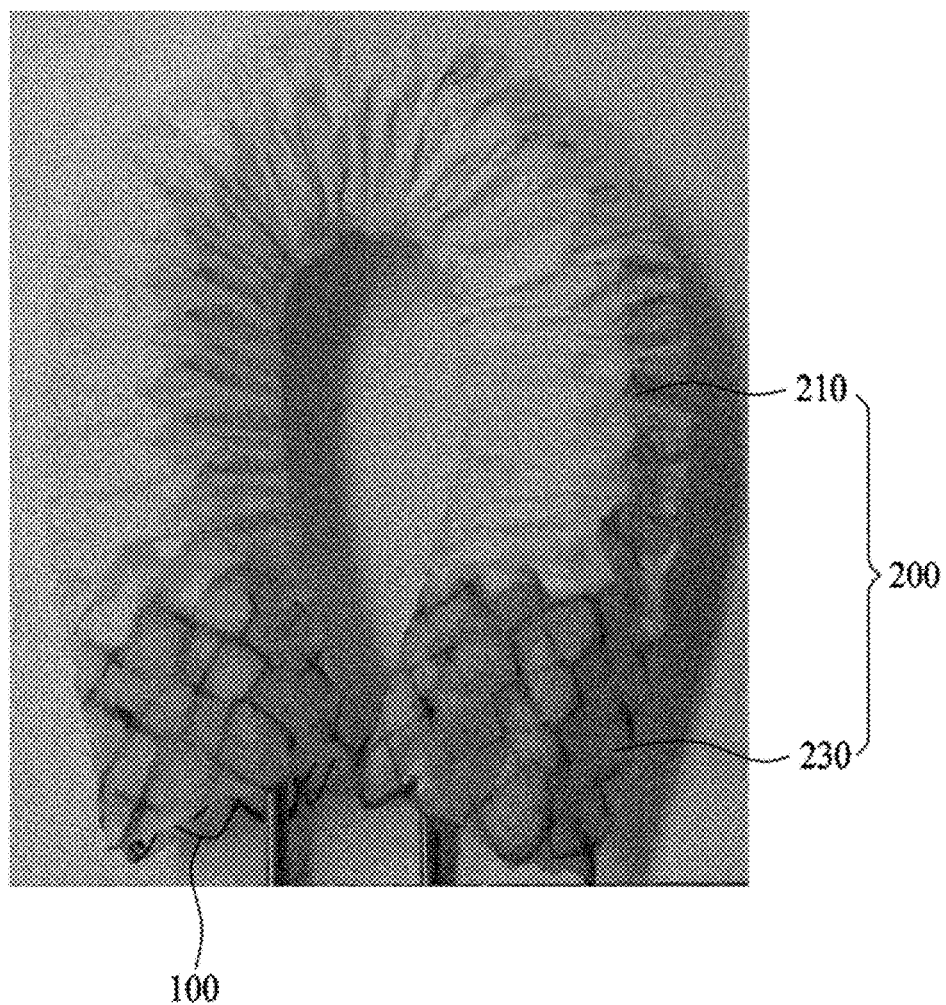

FIGS. 5 and 6 are pictures showing perspective views of a stent according to the present invention. According to a stent 10 manufactured in accordance with the process described above, as shown in FIGS. 1, 5, and 6, the holes at a predetermined portion of both ends of the stent main body 100 are closed by the primary coating layer 220 and the holes at the center portion of the stent main body 100 are closed by the film 210. The film 210 is relatively advantageous for bending the stent main body 100, as compared with the primary coating layer 220, so the stent 10 having the configuration described above, as shown in FIG. 6, can smoothly bend in accordance with the shape of the duct 500 or movement of a patient.

Although the primary coating layer 220 and the second coating layer 230 are formed only at both ends of the stent main body 100 in the process described above, depending on the use, it is apparent that at least any one of the primary coating layer 220 and the secondary coating layer 230 may be formed throughout the entire area of the stent main body 100.

Hereinafter, the shape of the external path 300 formed on the stent main body 100 is described in detail with reference to various embodiments.

First Embodiment

Figure 7:
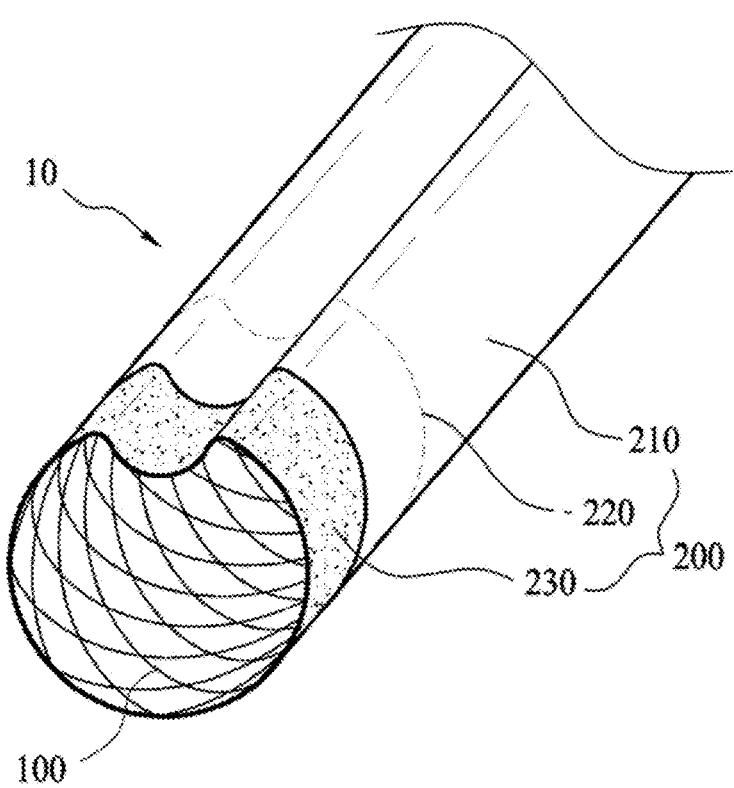
FIG. 7 is a partial perspective view of a stent according to a first embodiment of the present invention.

FIG. 7 is a partial perspective view of a stent according to a first embodiment of the present invention. The cross-section of the stent main body 100 is, as described above, generally formed in a circular shape. However, a recession may be formed on a side of the cross-section of the stent main body 100. The recession is formed along the longitudinal direction of the entire stent main body 100 to correspond to the cross-sectional shape. As described above, the recession formed along the longitudinal direction of the stent main body 100 is the external path 300.

It has generally a circular shape. However, a recession is formed on a side of the cross-section of the stent main body 100. The recession is formed along the longitudinal direction of the entire stent main body 100 to correspond to the cross-sectional shape. As described above, the recession formed along the longitudinal direction of the stent main body 100 is the external path 300.

The film 210 and the primary coating layer 200 are also formed maximally in close contact with the stent main body 100 so that the external path 300 is maintained even after the film 210 and the primary coating layer 220 are configured. Further, the edges of the recession may be rounded to prevent the edges of the recession from stimulating an installation portion.

Figure 8:
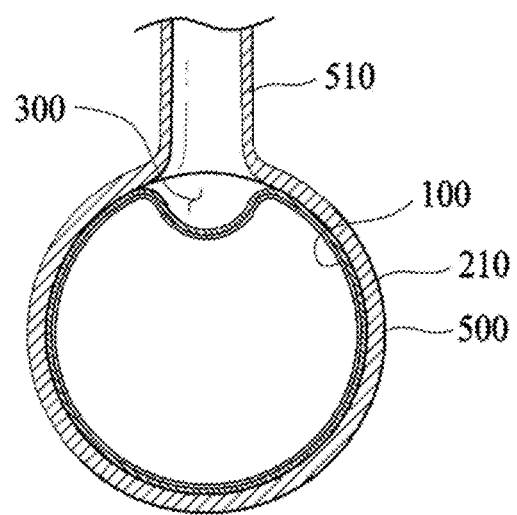
FIG. 8 is a cross-sectional view showing use of the stent according to the first embodiment of the present invention.

FIG. 8 is a cross-sectional view showing use of the stent according to the first embodiment of the present invention. As shown in FIG. 8, a divergent duct 510 such as an intrahepatic bile duct or a pancreatic duct from a cystic duct may be formed at a side of the duct 500 and body fluid discharged from the divergent duct 510 is supposed to flow through the duct 500. In this case, when a full-closed stent of the related art is used, the divergent duct 510 is clogged and cannot flow into the duct 500. However, since the external path 300 that is a recession is formed on the stent 10 according to the present invention, at a position corresponding to the divergent duct 510, body fluid discharging from the divergent duct 510 can flow through the duct 500 along the external path 300.

That is, body fluid can flow not only through the closed inside of the stent 10, but outside of the stent 10 through the external path 300. Accordingly, the body fluid discharged from the diverging duct 510 can easily flow into the duct 500.

Second Embodiment

Figure 9:
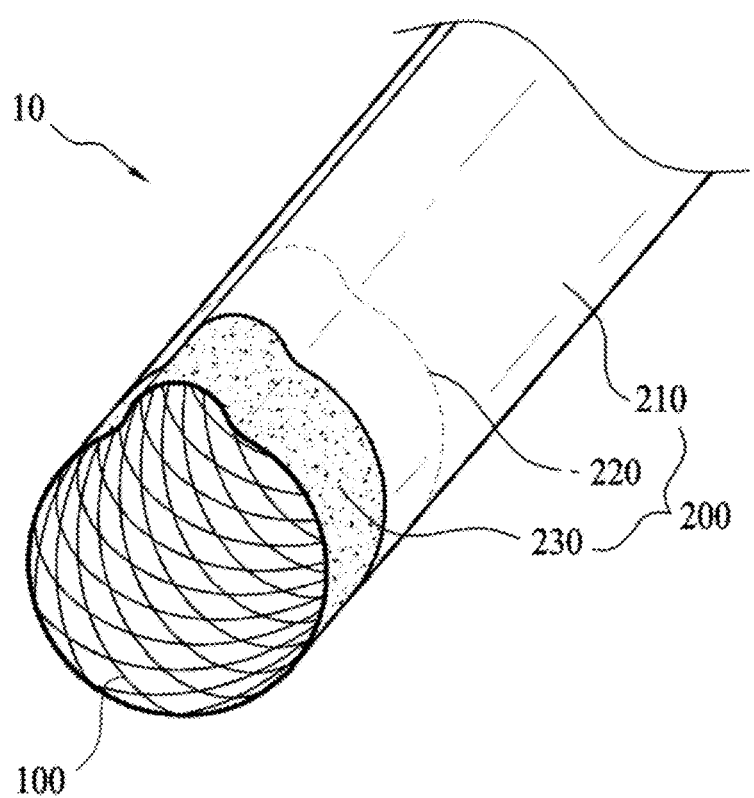
FIG. 9 is a partial perspective view of a stent according to a second embodiment of the present invention.

FIG. 9 is a partial perspective view of a stent according to a second embodiment of the present invention. A stent main body 100 according to the second embodiment of the present invention also has a generally circular cross-section, similar to the first embodiment. However, a projection is formed on a side of the cross-section of the stent main body 100. The projection is formed along the longitudinal direction of the entire stent main body 100 to correspond to the cross-sectional shape. The projection may be formed in a semi-circular or semi-elliptical shape without an edge to prevent stimulation on an installation portion, and the edge may be rounded.

As described above, when the stent 10 with the projection is inserted into the duct 400, a spare space is formed between the stent 10 and the duct 500 by the projection of the stent main body 100 and the spare space becomes an external path 300.

Similar to the first embodiment, the film 210 and the primary coating layer 200 may be maximally in close contact with the stent main body 100 so that the external path 300 is not clogged with the film 210 or the primary coating layer 220.

Figure 10:
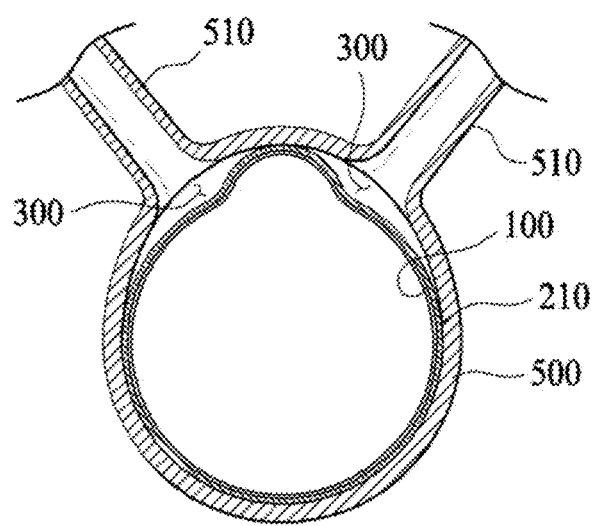
FIG. 10 is a cross-sectional view showing use of the stent according to the second embodiment of the present invention.

FIG. 10 is a cross-sectional view showing use of the stent according to the second embodiment of the present invention. As shown in FIG. 10, the stent 10 is inserted into the duct 500 so that a spare space formed by the projection is positioned at the position corresponding to the position where the diverging cut 510 connected to the duct 500 is formed. As described above, when the stent 10 is installed, a portion spaced without being in contact with the inner wall of the duct 500 by the projection on the outer peripheral surface of the stent 10 is formed along the longitudinal direction of the entire stent 10. The spare space formed by spacing in this way becomes the external path 300, so the body fluid discharged from the diverting duct 510 can flow into the duct 500 along the outside of the stent 10.

As described above, body fluid can flow not only through the closed inside of the stent 10 according to the second embodiment, but outside of the stent 10 along the external path 300. Accordingly, the body fluid discharged from the diverging conduct 510 can easily flow into the conduct 500.

Third Embodiment

Figure 11:
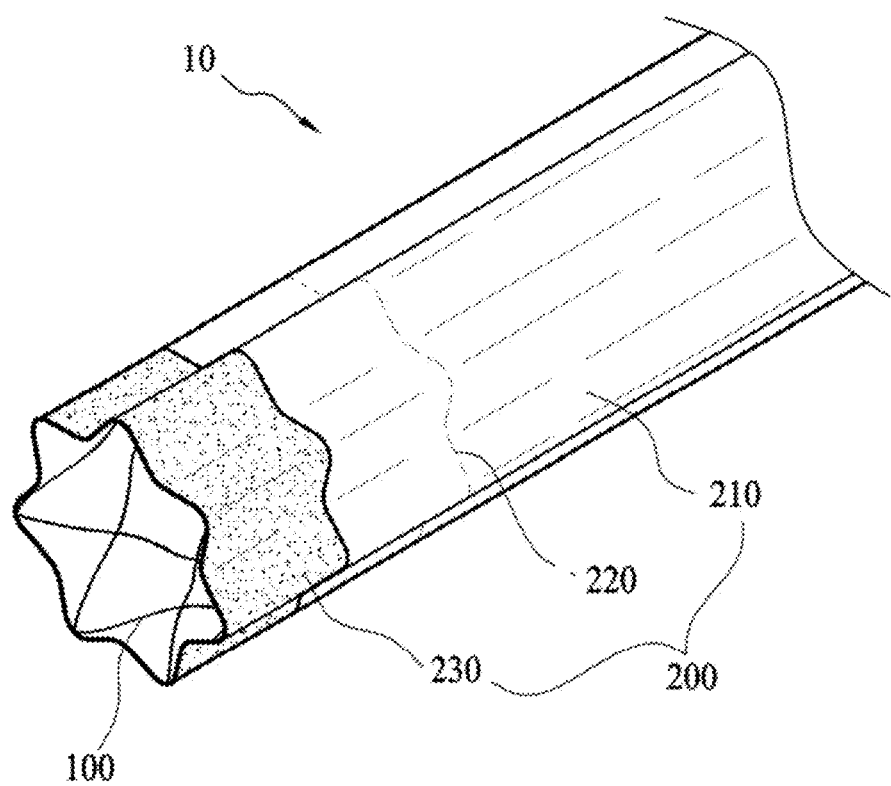
FIG. 11 is a partial perspective view of a stent according to a third embodiment of the present invention.
Figure 12:
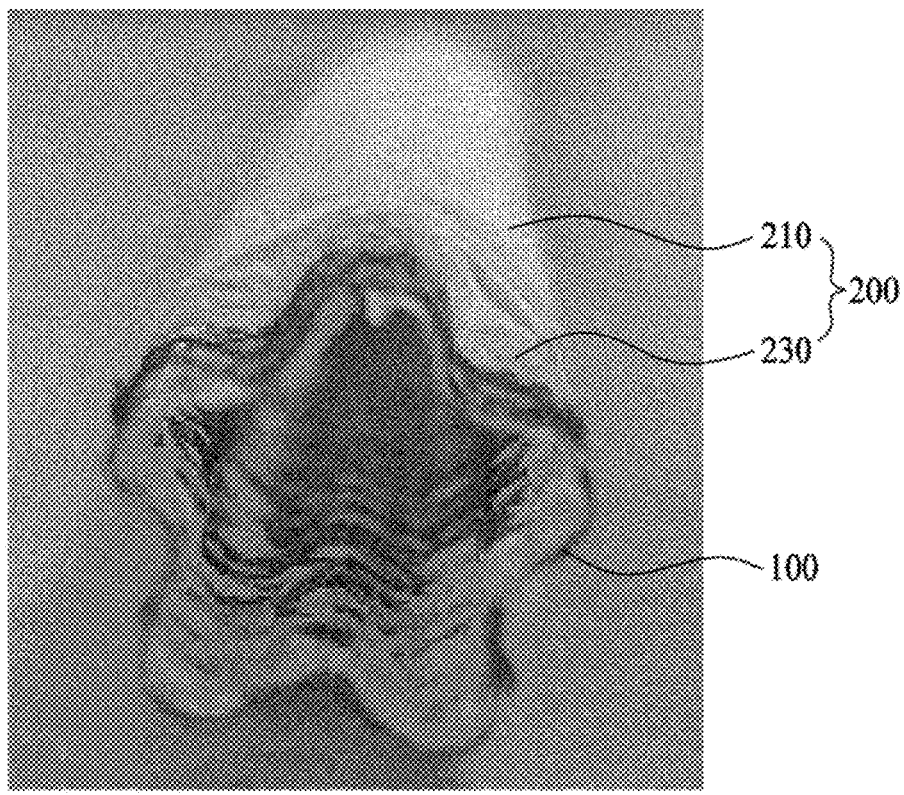
FIGS. 12 and 13 are pictures showing perspective views of the stent according to the third embodiment of the present invention.
Figure 13:
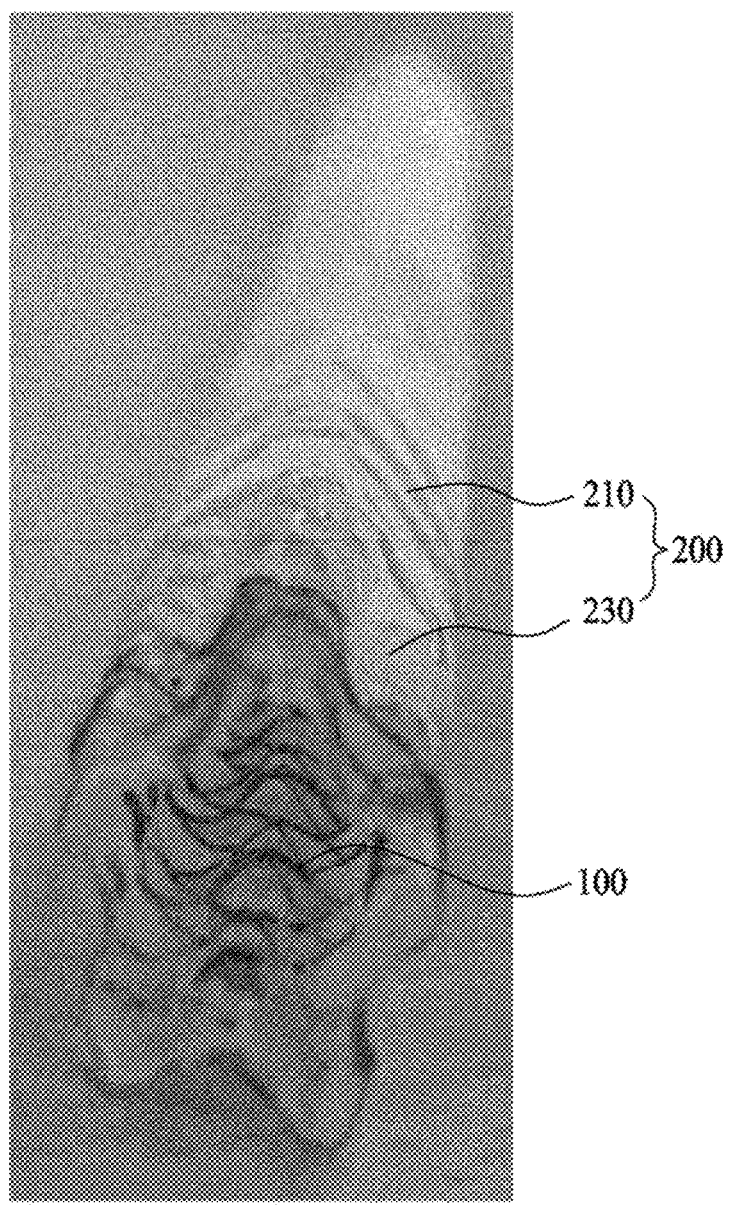

FIG. 11 is a partial perspective view of a stent according to a third embodiment of the present invention, and FIGS. 12 and 13 are pictures showing perspective views of the stent according to the third embodiment of the present invention. A stent 10 according to the third embodiment of the present invention, as shown in FIGS. 11 to 13, has a plurality of external paths 300. The external paths 300 may be formed in various shapes, including the shape of a star, by repeatedly arranging recessions and projections similar to those of the first embodiment and the second embodiment. That is, spare spaces generated by the difference in diameter due to the recessions and projections become the external paths 300. The recessions and the projections may be formed repeatedly with regular intervals, or may be non-uniformly formed, depending on the use.

Figure 14:
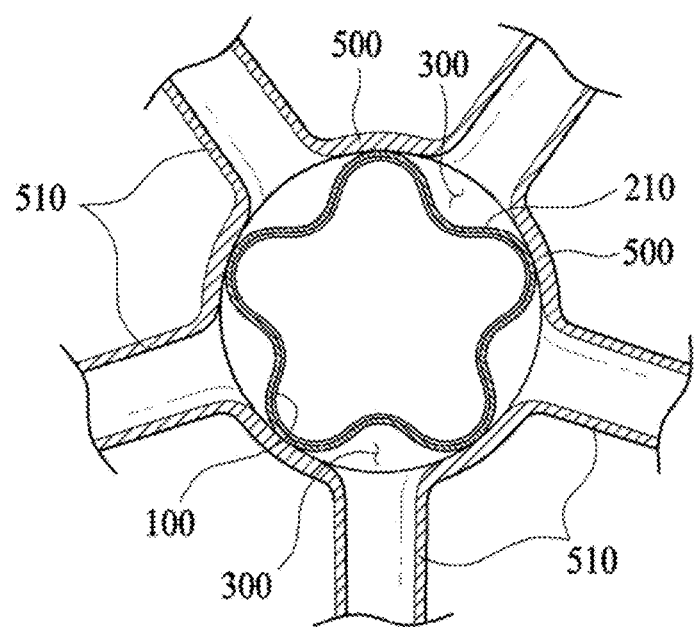
FIG. 14 is a cross-sectional view showing use of the stent according to the third embodiment of the present invention.

FIG. 14 is a cross-sectional view showing use of the stent according to the third embodiment of the present invention. The projections are brought in close contact with the inner wall of the duct 500 and the recessions are spaced from the inner wall of the duct 500, thereby forming the spare spaces. As described above, the spare spaces generated at the recessions become the external paths 300, so the body fluid discharged from the diverting duct 510 can flow into the duct 500 along the longitudinal direction of the stent 10.

Those skilled in the art would understand that the present invention may be implemented in various ways without changing the necessary features or the spirit of the present invention. Accordingly, it should be understood that the embodiments are fully an example and the present invention is not limited thereto. The scope of the present invention is defined by not the specification, but the following claims, and all of changes and modifications obtained from the meaning and range of claims and equivalent concepts should be construed as being included in the scope of the present invention.

The invention claimed is:

1. A stent comprising: a stent main body that has a first terminal end and a second terminal end disposed opposite the first terminal end, a longitudinal axis extending from the first terminal end to the second terminal end, a plurality of holes formed radially in the surface thereof and a circumferential part of which the inside is hollow; and
a cover that covers one side of the outer circumferential surface of the stent main body, wherein the stent main body has an external path that provides a channel through which the body fluid secreted from a diverging duct can flow along the longitudinal direction of the stent main body to the outside of the cover wherein the external path is formed by a recession on a side of the circumferential part of the stent main body and the recession is formed and extends substantially parallel to the longitudinal axis of the stent main body so that the body fluid secreted from the diverging duct flows through the recession, the recession extending from the first terminal end to the second terminal end.

2. The stent of claim 1, wherein the external path is formed by a projection on a side of the circumferential part of the stent main body and the projection is formed along the longitudinal direction of the stent main body so that the body fluid secreted from the diverging duct flows through a spaced space formed between the duct and the stent main body by the projection.

3. The stent of claim 1, wherein a plurality of external paths is provided.

4. A stent comprising: a stent main body that has a plurality of holes formed radially in the surface thereof and a circumferential part of which the inside is hollow, the stent body having a longitudinal axis extending from a first terminal end to a second terminal end; and
a cover that covers one side of the outer circumferential surface of the stent main body, wherein the stent main body has a plurality of external paths that provide channels through which the body fluid secreted from a diverging duct can flow along the longitudinal direction of the stent main body to the outside of the cover, the channels extending parallel to the longitudinal axis;

wherein the external paths are formed by recessions and projections repeatedly formed along the circumferential part of the stent main body and the recessions and the projections are formed along the longitudinal direction of the stent main body so that the body fluid secreted from the diverging duct flows through spaced spaces formed between the duct and the stent main body by the difference in diameter of the recessions and the projections.

5. A stent comprising:

a stent main body that has a plurality of holes formed radially in the surface thereof and a circumferential part of which the inside is hollow; and a cover that covers one side of the outer circumferential surface of the stent main body, wherein the stent main body has an external path that provides a channel through which the body fluid secreted from a diverging duct can flow along the longitudinal direction of the stent main body to the outside of the cover wherein at least any one end of both ends of the stent main body expands further than the center portion to prevent separation.

6. A stent comprising: a stent main body that has a plurality of holes formed radially in the surface thereof and a circumferential part of which the inside is hollow, the stent body having a longitudinal axis extending from a first terminal end to a second terminal end; and a cover that covers one side of the outer circumferential surface of the stent main body, the cover including a film for covering a side of the outer peripheral surface of the stent main body and a coating layer formed to coat both ends of the stent and fix the film to the stent main body, wherein the stent main body has an external path that provides a channel through which the body fluid secreted from a diverging duct can flow along the longitudinal direction of the stent main body to the outside of the cover, the channel extending parallel to the longitudinal axis.

7. The stent of claim 6, wherein the coating layer is formed at both ends of the stent main body to a depth where an end of the film is overlapped at a predetermined portion and is hardened to fix both ends of the film to the stent main body.

* * * * *